(12) United States Patent
Teamey et al.

(10) Patent No.: US 8,647,493 B2
(45) Date of Patent: *Feb. 11, 2014

(54) ELECTROCHEMICAL CO-PRODUCTION OF CHEMICALS EMPLOYING THE RECYCLING OF A HYDROGEN HALIDE

(71) Applicant: Liquid Light, Inc., Monmouth Junction, NJ (US)

(72) Inventors: Kyle Teamey, Washington, DC (US); Jerry J. Kaczur, North Miami Beach, FL (US)

(73) Assignee: Liquid Light, Inc., Monmouth Junction, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/724,878

(22) Filed: Dec. 21, 2012

(65) Prior Publication Data

US 2013/0134048 A1    May 30, 2013

Related U.S. Application Data

(60) Provisional application No. 61/703,229, filed on Sep. 19, 2012, provisional application No. 61/720,670,
(Continued)

(51) Int. Cl.
| | |
|---|---|
| C25B 1/00 | (2006.01) |
| C25B 3/00 | (2006.01) |
| C25C 1/24 | (2006.01) |
| C01B 7/01 | (2006.01) |
| C01B 7/19 | (2006.01) |
| C07C 5/31 | (2006.01) |
| C07C 15/02 | (2006.01) |

(52) U.S. Cl.
USPC ........... 205/555; 205/431; 205/440; 205/446; 205/448; 205/450; 205/462; 205/618; 205/619; 423/481; 423/483; 585/365; 585/400

(58) Field of Classification Search
USPC .......... 585/365, 400; 205/431, 440, 446, 448, 205/450, 462, 555, 618, 619; 423/481, 483
See application file for complete search history.

(56) References Cited

U.S. PATENT DOCUMENTS 3,019,256 A    1/1962    Dunn
(Continued)

FOREIGN PATENT DOCUMENTS

CA    1146120 A1    5/1983
(Continued)

OTHER PUBLICATIONS

Eggins, Brown, McNeill, and Grimshaw, Carbon Dioxide Fixation by Electrochemical Reduction in Water to Oxalate and Glyoxylate, Tetrahedron Letters vol. 29, No. 8, pp. 945-948, 1988, Pergamon Journals Ltd., Printed in Great Britain.
(Continued)

*Primary Examiner* — Edna Wong
(74) *Attorney, Agent, or Firm* — Suiter Swantz pc llo

(57) ABSTRACT

The present disclosure is a system and method for producing a first product from a first region of an electrochemical cell having a cathode and a second product from a second region of the electrochemical cell having an anode. The method may include a step of contacting the first region with a catholyte comprising carbon dioxide. The method may include another step of contacting the second region with an anolyte comprising a recycled reactant. The method may include a step of applying an electrical potential between the anode and the cathode sufficient to produce a first product recoverable from the first region and a second product recoverable from the second region. The second product may be removed from the second region and introduced to a secondary reactor. The method may include forming the recycled reactant in the secondary reactor.

18 Claims, 9 Drawing Sheets

Related U.S. Application Data filed on Oct. 31, 2012, provisional application No. 61/675,938, filed on Jul. 26, 2012, provisional application No. 61/703,158, filed on Sep. 19, 2012, provisional application No. 61/703,175, filed on Sep. 19, 2012, provisional application No. 61/703,231, filed on Sep. 19, 2012, provisional application No. 61/703,232, filed on Sep. 19, 2012, provisional application No. 61/703,234, filed on Sep. 19, 2012, provisional application No. 61/703,238, filed on Sep. 19, 2012, provisional application No. 61/703,187, filed on Sep. 19, 2012.

(56) References Cited

U.S. PATENT DOCUMENTS

| | | | |
|---|---|---|---|
| 3,293,292 | A | 12/1966 | Olivier et al. |
| 3,326,998 | A | 6/1967 | Reusser et al. |
| 3,341,615 | A | 9/1967 | Wulf et al. |
| 3,341,616 | A | 9/1967 | Vives |
| 3,352,935 | A | 11/1967 | Mahan |
| 3,361,653 | A | 1/1968 | Miller |
| 3,401,100 | A | 9/1968 | Macklin |
| 3,492,209 | A | 1/1970 | Miller |
| 3,560,354 | A | 2/1971 | Young |
| 3,607,962 | A | 9/1971 | Krekeler et al. |
| 3,636,159 | A | 1/1972 | Solomon |
| 3,720,591 | A | 3/1973 | Skarlos |
| 3,745,180 | A * | 7/1973 | Rennie ............... 552/304 |
| 3,764,492 | A | 10/1973 | Baizer et al. |
| 3,779,875 | A | 12/1973 | Michelet |
| 4,072,583 | A | 2/1978 | Hallcher et al. |
| 4,087,470 | A | 5/1978 | Suzuki |
| 4,088,682 | A | 5/1978 | Jordan |
| 4,162,948 | A | 7/1979 | Yagii et al. |
| 4,219,392 | A | 8/1980 | Halmann |
| 4,245,114 | A | 1/1981 | Peltzman |
| 4,256,550 | A | 3/1981 | Niinobe et al. |
| 4,343,690 | A * | 8/1982 | de Nora ............... 204/263 |
| 4,381,978 | A | 5/1983 | Gratzel et al. |
| 4,450,055 | A | 5/1984 | Stafford |
| 4,476,003 | A | 10/1984 | Frank et al. |
| 4,523,981 | A | 6/1985 | Ang et al. |
| 4,547,271 | A | 10/1985 | Bharucha et al. |
| 4,595,465 | A | 6/1986 | Ang et al. |
| 4,608,132 | A | 8/1986 | Sammells |
| 4,608,133 | A | 8/1986 | Morduchowitz et al. |
| 4,619,743 | A | 10/1986 | Cook |
| 4,661,422 | A | 4/1987 | Marianowski et al. |
| 4,673,473 | A | 6/1987 | Ang et al. |
| 4,702,973 | A | 10/1987 | Marianowski |
| 4,732,655 | A | 3/1988 | Morduchowitz et al. |
| 4,902,828 | A | 2/1990 | Wickenhaeuser et al. |
| 4,968,393 | A | 11/1990 | Mazur et al. |
| 5,074,974 | A | 12/1991 | Toomey, Jr. |
| 5,107,040 | A | 4/1992 | Repman et al. |
| 5,155,256 | A | 10/1992 | Chapman |
| 5,198,086 | A | 3/1993 | Chlanda et al. |
| 5,290,404 | A | 3/1994 | Toomey |
| 5,412,150 | A | 5/1995 | Wessel |
| 5,443,804 | A | 8/1995 | Parker et al. |
| 5,514,492 | A | 5/1996 | Marincic et al. |
| 5,654,493 | A | 8/1997 | Wessel |
| 5,804,045 | A | 9/1998 | Orillon et al. |
| 6,024,935 | A | 2/2000 | Mills et al. |
| 6,251,256 | B1 | 6/2001 | Blay et al. |
| 6,380,446 | B1 | 4/2002 | Drew et al. |
| 6,465,699 | B1 | 10/2002 | Grosso |
| 6,777,571 | B2 | 8/2004 | Chaturvedi et al. |
| 7,462,752 | B2 | 12/2008 | Fong et al. |
| 7,883,610 | B2 | 2/2011 | Monzyk et al. |
| 8,313,634 | B2 | 11/2012 | Bocarsly et al. |
| 2001/0026884 | A1 | 10/2001 | Appleby et al. |
| 2002/0022753 | A1 | 2/2002 | Drew et al. |
| 2006/0102468 | A1 | 5/2006 | Monzyk et al. |
| 2007/0004023 | A1 | 1/2007 | Trachtenberg et al. |
| 2007/0012577 | A1 | 1/2007 | Bulan et al. |
| 2007/0224479 | A1 | 9/2007 | Tadokoro et al. |
| 2008/0223727 | A1 | 9/2008 | Oloman et al. |
| 2008/0248350 | A1 | 10/2008 | Little et al. |
| 2008/0283411 | A1 | 11/2008 | Eastman et al. |
| 2008/0286643 | A1 | 11/2008 | Iwasaki |
| 2008/0296146 | A1 | 12/2008 | Toulhoat et al. |
| 2008/0314758 | A1 | 12/2008 | Grosso |
| 2009/0014336 | A1 | 1/2009 | Olah et al. |
| 2009/0030240 | A1 | 1/2009 | Olah et al. |
| 2010/0187123 | A1 | 7/2010 | Bocarsly et al. |
| 2010/0187125 | A1 | 7/2010 | Sandoval et al. |
| 2010/0191024 | A1 | 7/2010 | Uenveren et al. |
| 2010/0196800 | A1 | 8/2010 | Markoski et al. |
| 2010/0248042 | A1 | 9/2010 | Nakagawa et al. |
| 2010/0270167 | A1 | 10/2010 | McFarland |
| 2010/0330435 | A1 | 12/2010 | Nemeth et al. |
| 2011/0083968 | A1 | 4/2011 | Gillliam et al. |
| 2011/0114501 | A1 | 5/2011 | Teamey et al. |
| 2011/0114502 | A1 | 5/2011 | Cole et al. |
| 2011/0114503 | A1 | 5/2011 | Sivasankar et al. |
| 2011/0114504 | A1 | 5/2011 | Sivasankar et al. |
| 2011/0143929 | A1 | 6/2011 | Sato et al. |
| 2011/0186441 | A1 | 8/2011 | LaFrancois et al. |
| 2011/0226632 | A1 | 9/2011 | Cole et al. |
| 2011/0237830 | A1 | 9/2011 | Masel |
| 2012/0004448 | A1 | 1/2012 | Bhattacharyya et al. |
| 2012/0004449 | A1 | 1/2012 | Bhattacharyya |
| 2012/0004454 | A1 | 1/2012 | Bhattacharyya et al. |
| 2012/0018311 | A1 | 1/2012 | Yotsuhashi et al. |
| 2012/0043301 | A1 | 2/2012 | Arvin et al. |
| 2012/0215034 | A1 | 8/2012 | McFarland |
| 2012/0228147 | A1 | 9/2012 | Sivasankar et al. |
| 2012/0292196 | A1 * | 11/2012 | Albrecht et al. ............... 205/351 |
| 2012/0295172 | A1 | 11/2012 | Peled et al. |
| 2012/0298522 | A1 | 11/2012 | Shipchandler et al. |
| 2012/0329657 | A1 | 12/2012 | Eastman et al. |
| 2013/0062216 | A1 | 3/2013 | Yotsuhashi et al. |
| 2013/0098772 | A1 | 4/2013 | Bocarsly et al. |
| 2013/0105304 | A1 | 5/2013 | Kaczur et al. |
| 2013/0105330 | A1 * | 5/2013 | Teamey et al. ............... 205/349 |
| 2013/0118911 | A1 | 5/2013 | Sivasankar et al. |
| 2013/0134048 | A1 | 5/2013 | Teamey et al. |
| 2013/0134049 | A1 * | 5/2013 | Teamey et al. ............... 205/349 |
| 2013/0140187 | A1 | 6/2013 | Teamey et al. |
| 2013/0180863 | A1 | 7/2013 | Kaczur et al. |

FOREIGN PATENT DOCUMENTS

| | | | |
|---|---|---|---|
| CA | 1272161 A1 | 7/1990 | |
| CA | 2043256 A1 | 12/1991 | |
| CA | 2391938 A1 | 5/2001 | |
| DE | 1047765 A | 12/1958 | |
| DE | 2301032 A | 7/1974 | |
| FR | 853643 | 3/1940 | |
| GB | 1096847 A | 12/1967 | |
| GB | 1584524 A | 4/1977 | |
| GB | 2038335 A | 7/1980 | |
| GB | 2312218 A | 10/1997 | |
| JP | 64-015388 | 1/1989 | |
| WO | WO 9724320 A1 | 7/1997 | |
| WO | WO 0015586 A1 | 3/2000 | |
| WO | WO0138275 A1 | 5/2001 | |
| WO | WO 2004067673 A1 | 8/2004 | |
| WO | 2007041872 A1 | 4/2007 | |
| WO | WO 2007041872 A1 * | 4/2007 | ............... C25B 1/00 |
| WO | WO 2012046362 A1 | 4/2012 | |

OTHER PUBLICATIONS

M. Alvarez-Guerra et al., Conversion of carbon dioxide into formate using a continuous electrochemical reduction process in a lead cathode, Chem. Eng. J. (2012), http://dx.doi.org/10.1016/j.cej.2012.06.099.

Satoshi Kaneco, Kenji Iiba, Nobu-Hide Hiei, Kiyohisa Ohta, Takayuki Mizuno, and Tohru Suzuki, Electrochemical reduction of carbon dioxide to ethylene with high Faradaic efficiency at a Cu

(56) References Cited

OTHER PUBLICATIONS electrode in CsOH/methanol, Electrochimica Acta 44 (1999) 4701-4706.

Keith Scott, A Preliminary Investigation of the Simultaneous Anodic and Cathodic Production of Glyoxylic Acid, Electrochimica Acta, vol. 36, No. 9, pp. 1447-1452, 1991, Printed in Great Britain.

B. Eneau-Innocent et al., Electroreduction of carbon dioxide at a lead electrode in propylene carbonate: A spectroscopic study, Applied Catalysis B: Environmental 98 (2010) 65-71.

Kotaro Ogura et al., Selective Conversion of CO2 to Ethylene by the Electrolysis at a Three-Phase (Gas/Liquid/Solid) Interface in an Acidic Solution Containing Cupric Ions, Fuel Chemistry Division Preprints 2003, 48(1), 264.

S. Gambino and G. Silvestri, On the electrochemical reduction of carbon dioxide and ethylene, Tetrahedron Letters No. 32, pp. 3025-3028, 1973, Pergamon Press, Printed in Great Britain.

K.S. Udupa, G.S. Subramanian, and H.V.K. Udupa, The electrolytic reduction of carbon dioxide to formic acid, Electrochimica Acta, 1971, vol. 16, pp. 1593 to 1598, Pergamon Press, Printed in Northern Ireland.

Green et al., "Vapor-Liquid Equilibria of Formaldehyde-Methanol-Water", Industrial and Engineering Chemistry (Jan. 1955), vol. 47, No. 1, pp. 103-109.

Shibata et al., "Electrochemical Synthesis of Urea at Gas-Diffusion Electrodes Part VI. Simultaneous Reduction of Carbon Dioxide and Nitrite Ions with Various Metallophthalocyanine Catalysts". J. of Electroanalytical Chemistry (no month, 2001), vol. 507, pp. 177-184.

Jaaskelainen and Haukka, The Use of Carbon Dioxide in Ruthenium Carbonyl Catalyzed 1-hexene Hydroformylation Promoted by Alkali Metal and Alkaline Earth Salts, Applied Catalysis A: General, 247, 95-100 (2003).

Heldebrant et al., "Reversible Zwitterionic Liquids, The Reaction of Alkanol Guanidines, Alkanol Amidines, and Diamines wih CO2", Green Chem. (mo month, 2010), vol. 12, pp. 713-721.

Perez et al., "Activation of Carbon Dioxide by Bicyclic Amidines", J. Org. Chem. (no month, 2004), vol. 69, pp. 8005-8011.

Seshardi G., Lin C., Bocarsly A.B., A new homogeneous electrocatalyst for the reduction of carbon dioxide to methanol at low overpotential, Journal of Electroanalytical Chemistry, 1994, 372, pp. 145-150.

Seshadri et al., A New Homogeneous Electrocatalyst for the Reduction of Carbon Dioxide to Methanol at Low Overpotential, Journal of Electroanalytical Chemistry, 372 (1994), 145-50.

Green et al., Vapor-Liquid Equilibria of Formaldehyde-Methanol-Water, Industrial and Engineering Chemistry (Jan. 1955), vol. 47, No. 1, pp. 103-109.

Scibioh et al., Electrochemical Reduction of Carbon Dioxide: A Status Report, Proc Indian Natn Sci Acad (May 2004), vol. 70, A, No. 3, pp. 407-462.

Gennaro et al., Homogeneous Electron Transfer Catalysis of the Electrochemical Reduction of Carbon Dioxide. Do Aromatic Anion Radicals React in an Outer-Sphere Manner?, J. Am. Chem. Soc. (no month, 1996), vol. 118, pp. 7190-7196.

Perez et al., Activation of Carbon Dioxide by Bicyclic Amidines, J. Org. Chem. (no month, 2004), vol. 69, pp. 8005-8011.

Zaragoza Dorwald, Side Reactions in Organic Synthesis, 2005, Wiley-VCH Verlag GmbH & Co. KGaA, Weinheim, Preface. p. IX.

Liansheng et al, Journal of South Central University Technology, Electrode Selection of Electrolysis with Membrane for Sodium Tungstate Solution, 1999, 6(2), pp. 107-110.

Mahmood et al., Use of Gas-Diffusion Electrodes for High-Rate Electrochemical Reduction of Carbon Dioxide. II. Reduction at Metal Phthalocyanine-Impregnated Electrodes, J. of Appl. Electrochem. (no month, 1987), vol. 17, pp. 1223-1227.

Tanno et al., Electrolysis of Iodine Solution in a New Sodium Bicarbonate-Iodine Hybrid Cycle, International Journal of Hydrogen Energy (no month, 1984), vol. 9, No. 10, pp. 841-848.

Seshadri et al, "A new homogeneous catalyst for the reduction of carbon dioxide to methanol at low overpotential," Journal of Electroanalytical Chemistry, 372 (1994) 145-150.

Scibioh et al, "Electrochemical Reductin of Carbon Dioxide: A Status Report," Proc. Indian Natn Science Acad., 70, A, No. 3, May 2004, pp. 407-762.

Fukaya et al., "Electrochemical Reduction of Carbon Dioxide to Formate Catalyzed by Rh(bpy)3Cl3", Kagaku Gijutsu Kenkyusho Hokoku (no month, 1986), vol. 81, No. 5, pp. 255-258. 1-page abstract only.

Li et al., "The Electro-Reduction of Carbon Dioxide in a Continuous Reactor", J. of Applied Electrochemistry (no month, 2005), vol. 35, pp. 955-965.

Kaneco et al., "Electrochemical Reduction of Carbon Dioxide to Ethylene with High Faradaic Efficiency at a Cu Electrode in CsOH/Methanol", Electrochimica Acta (no month, 1999), vol. 44, pp. 4701-4706.

Kaneco et al., "Electrochemical Conversion of Carbon Dioxide to Formic Acid on Pb in KOH/Methanol Electrolyte at Ambient Temperature and Pressure", Energy (no month, 1998), vol. 23, No. 12, pp. 1107-1112.

Yuan et al., "Electrochemical Activation of Carbon Dioxide for Synthesis of Dimethyl Carbonate in an Ionic Liquid", Electrochimica Acta (no month, 2009), vol. 54, pp. 2912-2915.

U.S. Appl. No. 13/724,647, filed Dec. 21, 2012; Office Action mailed Oct. 17, 2013.

U.S. Appl. No. 13/787,481, filed Mar. 6, 2013; Office Action mailed Sep. 13, 2013.

U.S. Appl. No. 13/724,082, filed Dec. 21, 2012; Office Action mailed Aug. 12, 2013.

U.S. Appl. No. 13/724,522, filed Dec. 21, 2012; Office Action mailed Oct. 1, 2013.

U.S. Appl. No. 13/724,885, filed Dec. 21, 2012; Office Action mailed Aug. 21, 2013.

U.S. Appl. No. 13/724,231, filed Dec. 21, 2012; Office Action mailed Aug. 20, 2013.

Seshadri et al., "A new homogeneous electrocatalyst for the reduction of carbon dioxide to methanol at low overpotential", Journal of Electroanalytical Chemistry and Interfacial Electro Chemistry, Elsevier, Amsterdam, NL, vol. 372, No. 1-2, Jul. 8, 1994, pp. 145-150.

Hossain et al., "Palladium and cobalt complexes of substituted quinoline, bipyridine and phenanthroline as catalysts for electrochemical reduction of carbon dioxide", Electrochimica Acta, Elsevier Science Publishers, vol. 42, No. 16, Jan. 1, 1997, pp. 2577-2585.

Fisher et al., "Electrocatalytic reduction of carbon dioxide by using macrocycles of nickel and cobalt", Journal of the American Chemical Society, vol. 102, No. 24, Sep. 1, 1980, pp. 7361-7363.

Ishida et al., Selective Formation of HC00—In the Electrochemical CO2 Reduction Catalyzed by URU(BPY)2(CO)2 3/42+(BPY=2,2'-Bipyridine), Journal of the Chemical Society, Chemical Communications, Chemical Society, Letchworth, GB, Jan. 1, 1987, pp. 131-132.

Zhao et al., "Electrochemical reduction of supercritical carbon dioxide in ionic liquid 1-n-butyl-3-methylimidazolium hexafluorophosphate", Journal of Supercritical Fluids, PRA Press, US, vol. 32, No. 1-3, Dec. 1, 2004, pp. 287-291.

Hori et al, chapter on "Electrochemical CO2 Reduction on Metal Electrodes," in the book "Modern Aspects of Electrochemistry," vol. 42, pp. 106 and 107.

Czerwinski et al, "Adsorption Study of CO2 on Reticulated vitreous carbon (RVC) covered with platinum," Analytical Letters, vol. 18, Issue 14 (1985), pp. 1717-1722.

Hammouche et al, Chemical Catalysis of Electrochemical Reactions. Homogeneous Catalysis of the Electrochemical Reduction of Carbon Dioxide by Iron ("0") Porphyrins. Role of the Addition of Magnesium Cations. J. Am. Chem. Soc. 1991, 113, 8455-8466.

Hossain et al., Palladium and Cobalt Complexes of Substituted Quinoline, Bipyridine and Phenanthroline as Catalysts for Electrochemical Reduction of Carbon Dioxide, Electrochimica Acta (no month, 1997), vol. 42, No. 16, pp. 2577-2785.

Scibioh et al., "Electrochemical Reduction of Carbon Dioxide: A Status Report", Proc Indian Natn Sci Acad (May 2004), vol. 70, A, No. 3, pp. 407-462.

\* cited by examiner

ELECTROCHEMICAL CO-PRODUCTION OF CHEMICALS EMPLOYING THE RECYCLING OF A HYDROGEN HALIDE

CROSS-REFERENCE TO RELATED APPLICATIONS

The present application claims the benefit under 35 U.S.C. §119(e) of U.S. Provisional Application Ser. No. 61/720,670 filed Oct. 31, 2012, U.S. Provisional Application Ser. No. 61/703,229 filed Sep. 19, 2012 and U.S. Provisional Application Ser. No. 61/675,938 filed Jul. 26, 2012. Said U.S. Provisional Application Ser. No. 61/720,670 filed Oct. 31, 2012, U.S. Provisional Application Ser. No. 61/703,229 filed Sep. 19, 2012 and U.S. Provisional Application Ser. No. 61/675,938 filed Jul. 26, 2012 are incorporated by reference in their entireties.

The present application also claims the benefit under 35 U.S.C. §119(e) of U.S. Provisional Application Ser. No. 61/703,158 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,232, filed Sep. 19, 2012, U.S. Provisional Application Ser. No. 61/703,234, filed Sep. 19, 2012, U.S. Provisional Application Ser. No. 61/703,238 filed Sep. 19, 2012, U.S. Provisional Application Ser. No. 61/703,187 filed Sep. 19, 2012. The U.S. Provisional Application Ser. No. 61/703,158 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,232, filed Sep. 19, 2012, U.S. Provisional Application Ser. No. 61/703,234, filed Sep. 19, 2012, U.S. Provisional Application Ser. No. 61/703,238 filed Sep. 19, 2012 and U.S. Provisional Application Ser. No. 61/703,187 filed Sep. 19, 2012 are hereby incorporated by reference in their entireties.

The present application incorporates by reference co-pending U.S. patent application Ser. No. 13/724,339 filed on Dec. 21, 2012, U.S. patent application Ser. No. 13/724,647 filed on Dec. 21, 2012, U.S. patent application Ser. No. 13/724,231 filed on Dec. 21, 2012, U.S. patent application Ser. No. 13/724,807 filed on Dec. 21, 2012 U.S. patent application Ser. No. 13/724,996 filed on Dec. 21, 2012, U.S. patent application Ser. No. 13/724,719 filed on Dec. 21, 2012, U.S. patent application Ser. No. 13/724,082 filed on Dec. 21, 2012, and U.S. Patent application Ser. No. 13/724,768 filed on Dec. 21, 2012, now U.S. Pat. No. 8,444,844 in their entireties.

TECHNICAL FIELD

The present disclosure generally relates to the field of electrochemical reactions, and more particularly to methods and/or systems for electrochemical co-production of chemicals employing the recycling of a hydrogen halide.

BACKGROUND

The combustion of fossil fuels in activities such as electricity generation, transportation, and manufacturing produces billions of tons of carbon dioxide annually. Research since the 1970s indicates increasing concentrations of carbon dioxide in the atmosphere may be responsible for altering the Earth's climate, changing the pH of the ocean and other potentially damaging effects. Countries around the world, including the United States, are seeking ways to mitigate emissions of carbon dioxide.

A mechanism for mitigating emissions is to convert carbon dioxide into economically valuable materials such as fuels and industrial chemicals. If the carbon dioxide is converted using energy from renewable sources, both mitigation of carbon dioxide emissions and conversion of renewable energy into a chemical form that may be stored for later use will be possible.

SUMMARY OF THE PREFERRED EMBODIMENTS

The present disclosure includes a system and methods for producing a first product from a first region of an electrochemical cell having a cathode and a second product from a second region of the electrochemical cell having an anode. The method may include a step of contacting the first region with a catholyte comprising carbon dioxide. The method may include another step of contacting the second region with an anolyte comprising a recycled reactant. The method may include a step of applying an electrical potential between the anode and the cathode sufficient to produce a first product recoverable from the first region and a second product recoverable from the second region. The second product may be removed from the second region and introduced to a secondary reactor. The method may include forming the recycled reactant in the secondary reactor.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Referring generally to FIGS. 1-8, systems and methods of electrochemical co-production of products with a recycled halogen halide fed to an anode are disclosed. It is contemplated that the electrochemical co-production of products may include production of a first product, such as reduction of carbon dioxide to carbon-based products including one, two, three, and four carbon chemicals, at a cathode side of an electrochemical cell with co-production of a second product, such as a halide (e.g., $X_2$, where X is F, Cl, Br, I, or mixtures thereof), at the anode of the electrochemical cell where the anolyte comprises a recycled reactant, where the recycled reactant is preferably HX.

Before any embodiments of the disclosure are explained in detail, it is to be understood that the embodiments may not be limited in application per the details of the structure or the function as set forth in the following descriptions or illustrated in the figures. Different embodiments may be capable of being practiced or carried out in various ways. Also, it is to be understood that the phraseology and terminology used herein is for the purpose of description and should not be regarded as limiting. The use of terms such as "including," "comprising," or "having" and variations thereof herein are generally meant to encompass the item listed thereafter and equivalents thereof as well as additional items. Further, unless otherwise noted, technical terms may be used according to conventional usage. It is further contemplated that like reference numbers may describe similar components and the equivalents thereof.

Figure 1:
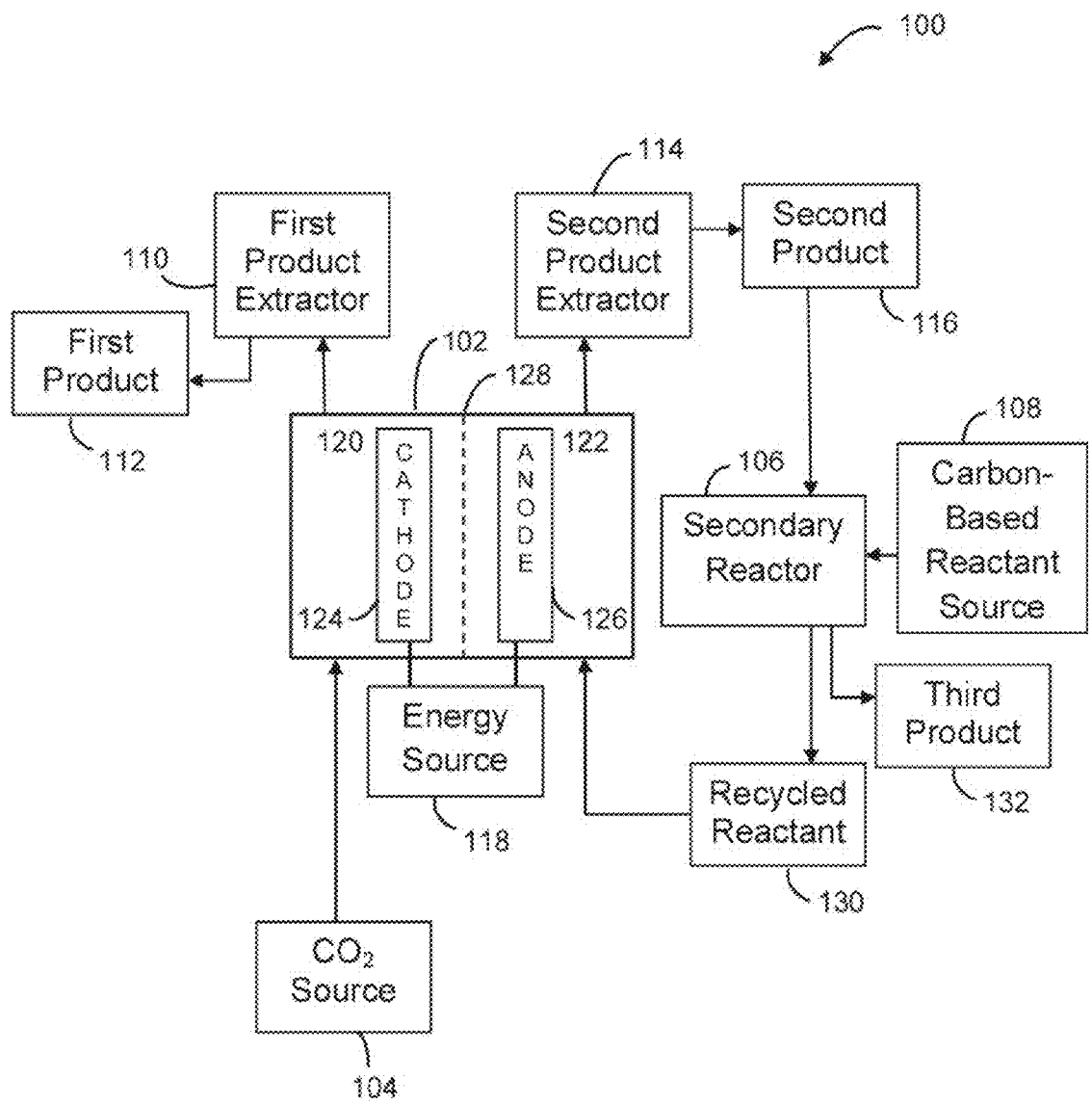
FIG. 1 is a block diagram of a system in accordance with an embodiment of the present disclosure.

Referring to FIG. 1, a block diagram of a system 100 in accordance with an embodiment of the present disclosure is shown. System (or apparatus) 100 generally includes an electrochemical cell (also referred as a container, electrolyzer, or cell) 102, a carbon dioxide source 104, a secondary reactor 106, a carbon-based reactant source 108, a first product extractor 110 (configured to extract a first product 112), a second product extractor 114 (configured to extract a second product 116), and an energy source 118.

Electrochemical cell 102 may be implemented as a divided cell. The divided cell may be a divided electrochemical cell and/or a divided photo-electrochemical cell. Electrochemical cell 102 may include a first region 120 and a second region 122. First region 120 and second region 122 may refer to a compartment, section, or generally enclosed space, and the like without departing from the scope and intent of the present disclosure. First region 120 may include a cathode 124. Second region 122 may include an anode 126. First region 120 may include a catholyte whereby carbon dioxide is dissolved in the catholyte. Second region 122 may include an anolyte which may include a recycled reactant (e.g., HX, where X is F, Cl, Br, I and mixtures thereof). A source of HX may be operably connected to second region 122. Energy source 118 may generate an electrical potential between the anode 126 and the cathode 124. The electrical potential may be a DC voltage. Energy source 118 may be configured to supply a variable voltage or constant current to electrochemical cell 102. A separator 128 may selectively control a flow of ions between the first region 120 and the second region 122. Separator 128 may include an ion conducting membrane or diaphragm material.

Electrochemical cell 102 is generally operational to reduce carbon dioxide in the first region 120 to a first product 112 recoverable from the first region 120 while producing a second product 116 recoverable from the second region 122. Cathode 124 may reduce the carbon dioxide into the first product 112 that may include one or more compounds. Examples of the first product 112 recoverable from the first region 120 by the first product extractor 110 may include carbon monoxide, formic acid, formaldehyde, methanol, methane, oxalate, oxalic acid, glyoxylic acid, glyoxylate, glycolic acid, glycolate, glyoxal, glycolaldehyde, ethylene glycol, acetic acid, acetate, acetaldehyde, ethanol, ethane, ethylene, lactic acid, lactate, propanoic acid, propionate, acetone, isopropanol, 1-propanol, 1,2-propylene glycol, propane, propylene, 1-butanol, 2-butanone, 2-butanol, butane, butene, a carboxylic acid, a carboxylate, a ketone, an aldehyde, and an alcohol.

Carbon dioxide source 104 may provide carbon dioxide to the first region 120 of electrochemical cell 102. In some embodiments, the carbon dioxide is introduced directly into the region 120 containing the cathode 124. It is contemplated that carbon dioxide source 104 may include a source of a mixture of gases in which carbon dioxide has been separated and filtered from the gas mixture.

First product extractor 110 may include an organic product and/or inorganic product extractor. First product extractor 110 is generally operational to extract (separate) the first product 112 from the first region 120. The extracted first product 112 may be presented through a port of the system 100 for subsequent storage and/or consumption by other devices and/or processes.

The anode side of the reaction occurring in the second region 122 may include a recycled reactant 130, may be a gas phase, liquid phase, or solution phase reactant, supplied to the second region 122. The second product 116 recoverable from the second region 122 may be derived from the oxidation of HX. Second product extractor 114 may extract the second product 116 from the second region 122. Examples of the second product 116 recoverable from the second region 122 by the second product extractor 114 may include $F_2$, $Cl_2$, $Br_2$, and $I_2$, and mixtures thereof.

The extracted second product 116 may be presented through a port of the system 100 for subsequent storage and/or consumption by other devices and/or processes. It is contemplated that first product extractor 110 and/or second product extractor 114 may be implemented with electrochemical cell 102, or may be remotely located from the electrochemical cell 102. Additionally, it is contemplated that first product extractor 110 and/or second product extractor 114 may be implemented in a variety of mechanisms and to provide desired separation methods, such as fractional distillation, without departing from the scope and intent of the present disclosure.

Furthermore, second product 116 may be presented to another reactor, such as a secondary reactor 106, where the recycled reactant 130 is a product of a reaction of the second product 116 recovered from the second region 118 of the electrochemical cell 102 with a carbon-based reactant from the carbon-based reactant source 108. For instance, the secondary reactor 106 may include the carbon-based reactant therein to react with the second product 116. The carbon-based reactant may include, for example, an alkane, an alkene, an aromatic, or another organic compound. A third product 132 produced by secondary reactor 106 as an additional product of a reaction at secondary reactor 106 may include a halogenated organic compound or halogenated intermediate that may be further converted to another product. Recycled reactant 130 may be recycled back to the second region 122 as an input feed to the second region 122 of electrochemical cell 102. It is contemplated that an additional source of recycled reactant may be further supplied as an input feed to the second region 122 of the electrochemical cell 102 without departing from the scope and intent of the present disclosure.

Through the co-production of the first product 112 and the second product 116, the overall energy requirement for making each of the first product 112 and second product 116 may be reduced by 50% or more. In addition, electrochemical cell 102 may be capable of simultaneously producing two or more products with high selectivity. The organic chemical partially oxidized in the reaction may serve as the source of hydrogen for the reduction of carbon dioxide. The organic may thereby be indirectly oxidized by carbon dioxide while the carbon dioxide is reduced by the organic such that two or more products are made simultaneously. Advantageously, the halogen may be employed to partially oxidize an organic and provide hydrogen halide which may be recycled to the electrochemical cell 102 and used for the reduction of $CO_2$.

Figure 2A:
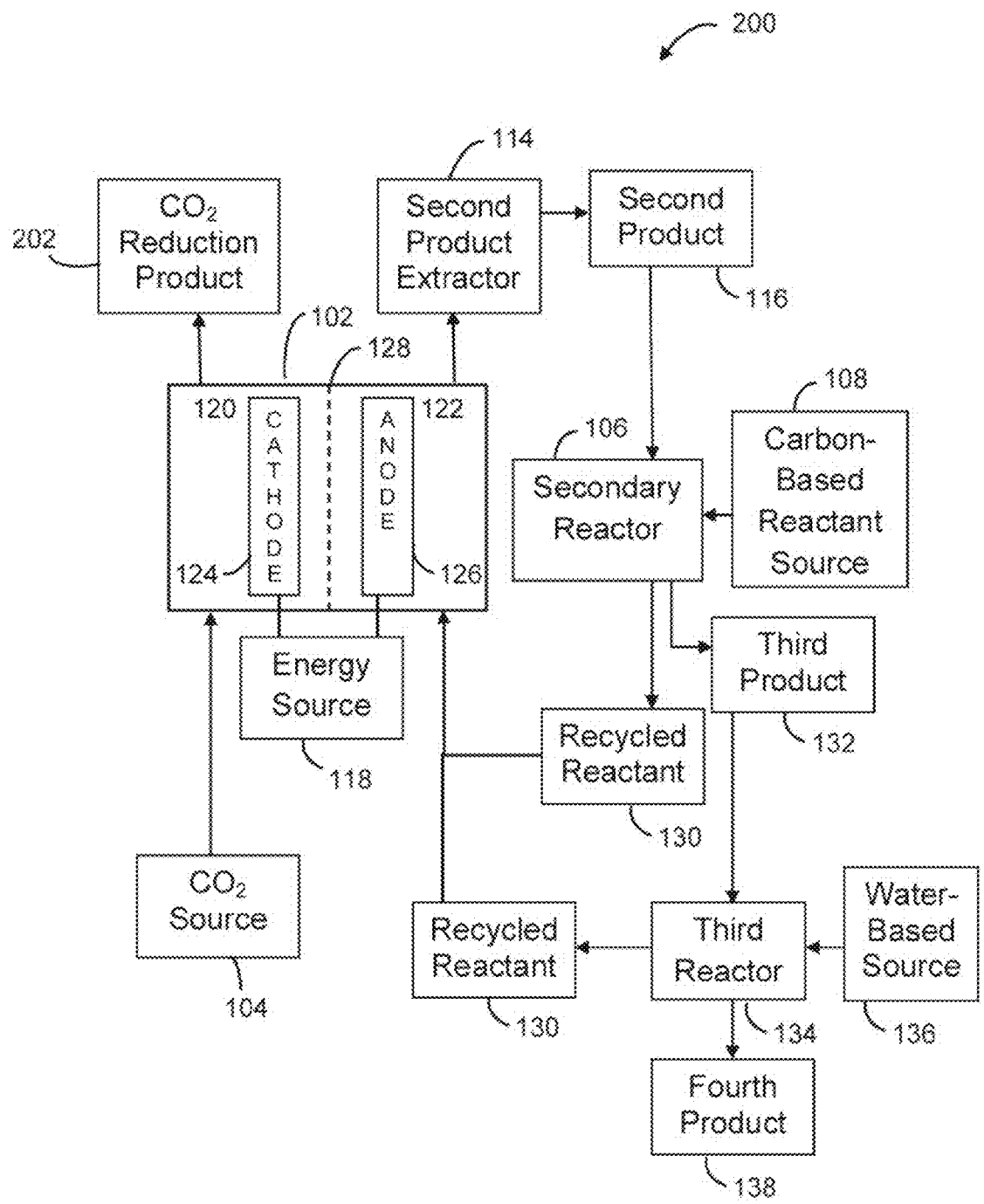
FIG. 2A is a block diagram of a system in accordance with another embodiment of the present disclosure.

A preferred embodiment of the present disclosure may include production of organic chemicals, such as carbon dioxide reduction products, at the cathode while simultaneously using a hydrogen halide feed to the anode for production of $X_2$, which is subsequently used to generate additional products. Referring to FIG. 2A, a system 200 for co-production of a carbon dioxide reduction product 202 and a fourth product 138, preferably one or more of an alkene, an alcohol, and an olefin, is shown. Examples of some possible fourth products and the organic compound from which they are derived are in Table 1 below. The oxidation of the recycled reactant 130, preferably HX, where X is F, Cl, Br, I, and mixtures thereof, in the second region 122 produces protons and electrons that are utilized to reduce carbon dioxide in the first region 120. The oxidation of the recycled reactant 130 may produce the second product 116, which is preferably $X_2$, which may be reacted in the secondary reactor 106 to selectively produce the third product 132, preferably a halogenated compound. The third product 132 may be isolated or it may be supplied to a third reactor 134 for additional reactions to generate a fourth product 138 and the recycled reactant 130. Third reactor 134 may include a feed of water, or hydroxide ion, 136 to produce an alkene or alcohol and the recycled reactant 130. Alternatively, the third reactor 134 does not receive water, or hydroxide ion, as a reactant and instead produces the recycled reactant and one or more of an alkyne and an alkene. The recycled reactant 130 formed in the third reactor 134 may be recycled back to the second region 122 as an input feed to the second region 122 of electrochemical cell 102 either as a pure anhydrous gas or in a liquid phase.

TABLE 1

| Organic Feed | Oxidation Product(s) |
| --- | --- |
| Methane | Methanol, formaldehyde, formic acid, ethylene, longer chain compounds such as ethane |
| Ethane | Ethanol, acetaldehyde, acetic acid, ethylene glycol, ethylene, acetylene, longer chain compounds such as butane |
| Ethene (Ethylene) | Acetylene |
| Propane | Propanol, isopropanol, propanone, acetone, propanoic acid, lactic acid, propylene glycol, propylene |
| Butane | Butanol, butane, butadiene |
| Isobutane | Isobutanol, isobutylene |
| Benzene | Phenol |
| Toluene | Benzyl alcohol, benzyl aldehyde, benzoic acid |
| Xylene | Terephthalic acid, isophthalic acid, phthalic acid |

Figure 2B:
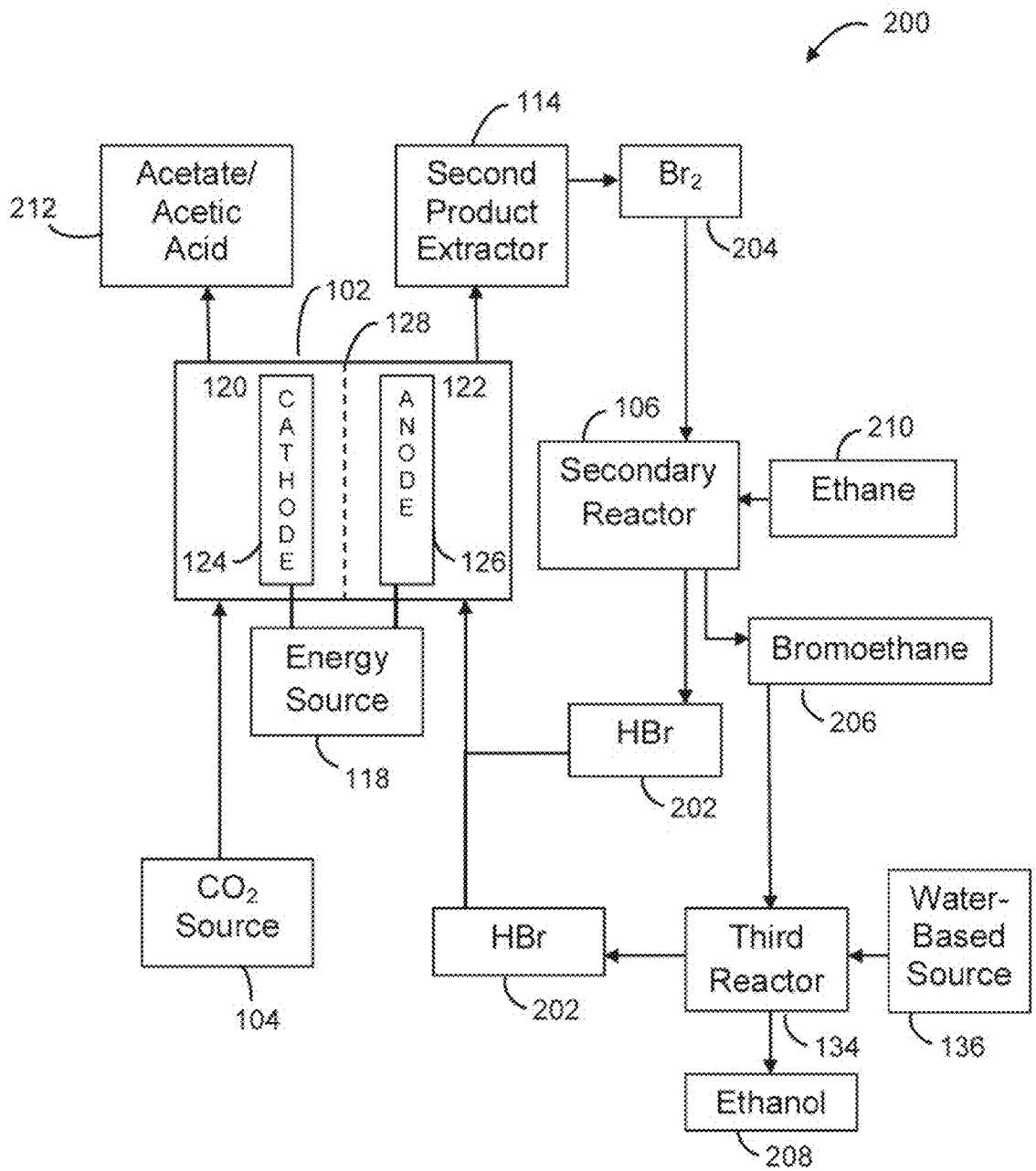
FIG. 2B is a block diagram of a system in accordance with an additional embodiment of the present disclosure.

Referring to FIG. 2B, a block diagram of a system 200 in accordance with an additional embodiment of the present disclosure is shown. Similar to the embodiment shown in FIG. 2A, FIG. 2B is a block diagram of a system in accordance with an additional embodiment of the present disclosure wherein the recycled reactant 130 is hydrogen bromide (HBr) 202, the second product 116 is $Br_2$ 204, the third product 132 is bromoethane 206, and the fourth product 138 is ethanol 208. Bromine ($Br_2$) may be supplied to secondary reactor 106 and reacted with ethane 210 to produce HBr 202, which is recycled as an input feed to the second region 122, and bromoethane 206. Bromoethane 206 may be supplied to third reactor 134 and reacted with water from water source 136 to produce HBr 202, which is recycled as an input feed to the second region 122, and ethanol 208. In another embodiment of the disclosure, water is not reacted in third reactor 134, and the bromoethane 206 is reacted to produce HBr 202 and one or more of an alkyne or an alkene such as ethylene. The carbon dioxide reduction product of FIG. 2B preferably includes one or more of acetate and acetic acid 212. When the carbon dioxide reduction product is acetic acid and when ethanol 208 is produced in third reactor 134, then the molar ratios of the product may be 1 acetic acid:4 ethanol because acetic acid production from $CO_2$ is an 8 electron process and ethanol from ethane is a two electron process. The mass ratios may be 1:3.

Figure 3:
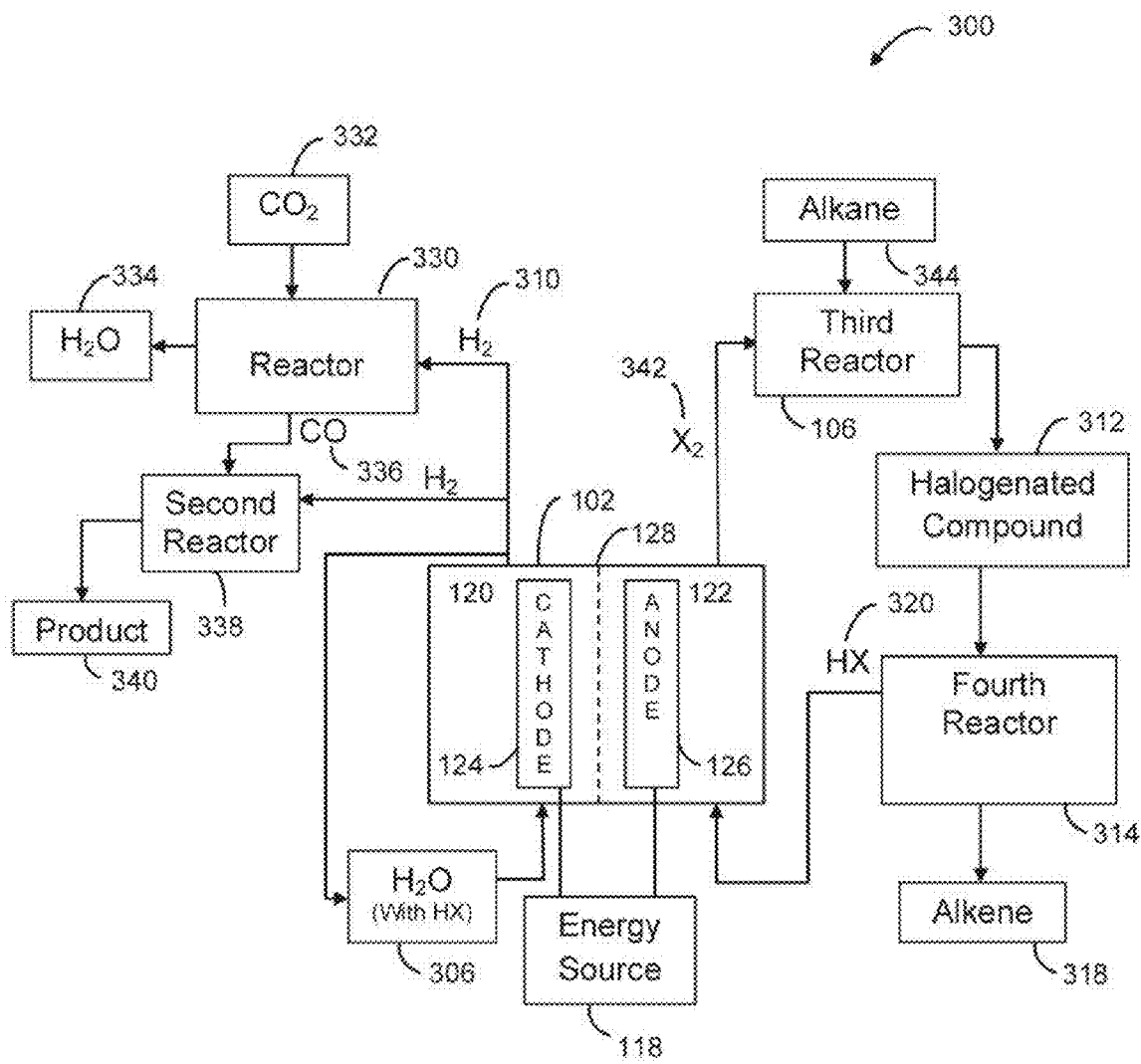
FIG. 3 is a block diagram of a system in accordance with an additional embodiment of the present disclosure.
Figure 4:
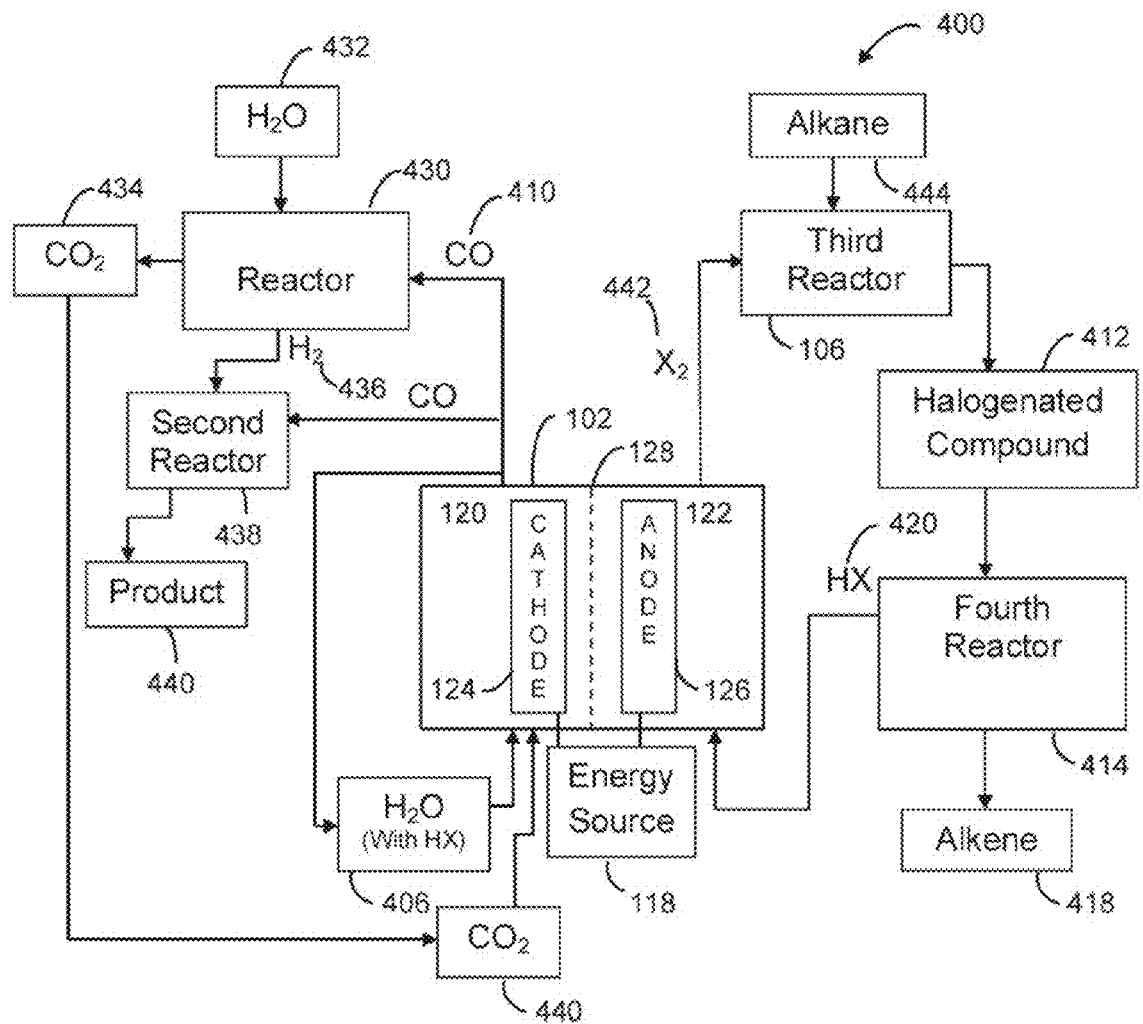
FIG. 4 is a block diagram of a system in accordance with an additional embodiment of the present disclosure.

Referring to FIGS. 3 and 4 with block diagrams of systems 300, 400 in accordance with additional embodiments of the present disclosure are shown. Systems 300, 400 provide additional embodiments to systems 100, 200 of FIGS. 1-2 to co-produce a first product and second product.

Referring specifically to FIG. 3, first region 120 of electrochemical cell 102 may produce a first product of $H_2$ 310 which is combined with carbon dioxide 332 in a reactor 330 which may perform a reverse water gas shift reaction. This reverse water gas shift reaction performed by reactor 330 may produce water 334 and carbon monoxide 336. Carbon monoxide 336 along with $H_2$ 310 may be combined at second reactor 338. Reactor 338 may cause a reaction by utilizing $H_2$ 310 from the first region 120 of the electrochemical cell 102, such as a Fischer-Tropsch-type reaction, to reduce carbon monoxide to a product 340. Product 340 may include methane, methanol, hydrocarbons, glycols, and olefins. Water 306, which may include a hydrogen halide, may be an additional product produced by the first region 120 and may be recycled as an input feed to the first region 120. Second reactor 338 may also include transition metals such as iron, cobalt, and ruthenium as well as other transition metal oxides as catalysts, on inorganic support structures that may promote the reaction of CO with hydrogen at lower temperatures and pressures.

Second region 122 may co-produce $X_2$ 342, where X is F, Cl, Br, I, and mixtures thereof. In an embodiment, the $X_2$ is $Br_2$. The $X_2$ 342 may be introduced to the third reactor 106, which may have a feed input of an alkane, an alkene, an alkyne, and an aromatic compound 344, for production of a halogenated compound 312. In an embodiment, the alkane 344 is ethane and the halogenated compound 312 is bromoethane. Halogenated compound 312 may be isolated, or may be supplied to a fourth reactor 314 to generate products such as an alkene 318 and a hydrogen halide recycled reactant 320, which is recycled back as an input feed to the second region 122. In an embodiment, the alkene 318 is ethylene and the hydrogen halide recycled reactant 320 is hydrogen bromide (HBr). It is contemplated that alkane 344 may be other types of carbon-based reactants, including various types of alkanes, alkenes, or aromatic compounds while halogenated compound 312 may also refer to any type of halogenated compound that may be supplied to a fourth reactor 314 to produce various types of alkenes, alcohols, aldehydes, ketones, glycols, or olefins without departing from the scope or intent of the present disclosure.

Referring to FIG. 4, first region 120 of electrochemical cell 102 may produce a first product of carbon monoxide 410 which is combined with water 432 in a reactor 430 which may perform a water gas shift reaction. This water gas shift reaction performed by reactor 430 may produce carbon dioxide 434 and $H_2$ 436. Carbon monoxide 410 and $H_2$ 436 may be combined at second reactor 438. Second reactor 438 may cause a reaction, such as a Fischer-Tropsch-type reaction, to reduce carbon monoxide to a product 440. Product 440 may include methane, methanol, hydrocarbons, glycols, or olefins by utilizing $H_2$ 436 from the water gas shift reaction. Carbon dioxide 434 may be a byproduct of water gas shift reaction of reactor 430 and may be recycled as an input feed to the first region 120 Water 406, which may include a hydrogen halide, may be an additional product produced by the first region 120 and may be recycled as another input feed to the first region 120. Second reactor 438 may also include transition metals and their oxides, such as iron and copper oxides as catalysts, on inorganic support structures that may promote the reaction of CO with hydrogen at lower temperatures and pressures.

Second region 122 may co-produce $X_2$ 442, where X is F, Cl, Br, I and mixtures thereof. In an embodiment, the $X_2$ is $Br_2$. The $X_2$ 442 may be introduced to the third reactor 106, which may have a feed input of an alkane, an alkene, an alkyne, and an aromatic compound 444, for production of a halogenated compound 412. In an embodiment, an alkane 444 is ethane and the halogenated compound 412 is bromoethane. Halogenated compound 412 may be isolated, or may be supplied to a fourth reactor 414 to generate byproducts such as an alkene 418 and a hydrogen halide recycled reactant 420, which is recycled back as an input feed to the second region 122. In an embodiment, the alkene 418 is ethylene and the hydrogen halide recycled reactant 420 is hydrogen bromide (HBr). It is contemplated that alkane 444 may be other types of carbon-based reactants, including various types of alkanes, alkenes, or aromatic compounds while halogenated compound 412 may also refer to any type of halogenated compound that may be supplied to a fourth reactor 414 to produce various types of alkenes, alkynes, alcohols, aldehydes, ketones, glycols, or olefins without departing from the scope or intent of the present disclosure.

It is contemplated that reactions occurring at the first region 120 may occur in a catholyte which may include water, methanol, acetonitrile, propylene carbonate, ionic liquids, or other catholytes. They may also occur in the gas phase, though liquid phase may be preferred. The reactions occurring at the second region 122 may be in a gas phase or may occur in liquid phase, for example, in an aqueous or non-aqueous solution.

It is further contemplated that the structure and operation of the electrochemical cell 102 may be adjusted to provide desired results. For example, the electrochemical cell 102 may operate at higher pressures, such as pressure above atmospheric pressure which may increase current efficiency and allow operation of the electrochemical cell at higher current densities.

Additionally, the cathode 124 and anode 126 may include a high surface area electrode structure with a void volume which may range from 30% to 98%. The electrode void volume percentage may refer to the percentage of empty space that the electrode is not occupying in the total volume space of the electrode. The advantage in using a high void volume electrode is that the structure has a lower pressure drop for liquid flow through the structure. The specific surface area of the electrode base structure may be from 2 $cm^2/cm^3$ to 500 $cm^2/cm^3$ or higher. The electrode specific surface area is a ratio of the base electrode structure surface area divided by the total physical volume of the entire electrode. It is contemplated that surface areas also may be defined as a total area of the electrode base substrate in comparison to the projected geometric area of the current distributor/conductor back plate, with a preferred range of 2× to 1000× or more. The actual total active surface area of the electrode structure is a function of the properties of the electrode catalyst deposited on the physical electrode structure which may be 2 to 1000 times higher in surface area than the physical electrode base structure.

Cathode 124 may be selected from a number of high surface area materials to include copper, stainless steels, transition metals and their alloys and oxides, carbon, and silicon, which may be further coated with a layer of material which may be a conductive metal or semiconductor. The base structure of cathode 124 may be in the form of fibrous, reticulated, or sintered powder materials made from metals, carbon, or other conductive materials including polymers. The materials may be a very thin plastic screen incorporated against the cathode side of the membrane to prevent the membrane 128 from directly touching the high surface area cathode structure. The high surface area cathode structure may be mechanically pressed or physically bonded against a cathode current distributor back plate, which may be composed of material that has the same surface composition as the high surface area cathode.

In addition, cathode 124 may be a suitable conductive electrode, such as Al, Au, Ag, Bi, C, Cd, Co, Cr, Cu, Cu alloys (e.g., brass and bronze), Ga, Hg, In, Mo, Nb, Ni, $NiCo_2O_4$, Ni alloys (e.g., Ni 625, NiHX), Ni—Fe alloys, Pb, Pd alloys (e.g., PdAg), Pt, Pt alloys (e.g., PtRh), Rh, Sn, Sn alloys (e.g., SnAg, SnPb, SnSb), Ti, V, W, Zn, stainless steel (SS) (e.g., SS 2205, SS 304, SS 316, SS 321), austenitic steel, ferritic steel, duplex steel, martensitic steel, Nichrome (e.g., NiCr 60:16 (with Fe)), elgiloy (e.g., Co—Ni—Cr), degenerately doped p-Si, degenerately doped p-Si:As, degenerately doped p-Si:B, degenerately doped n-Si, degenerately doped n-Si:As, and degenerately doped n-Si:B. These metals and their alloys may also be used as catalytic coatings on the various metal substrates. Other conductive electrodes may be implemented to meet the criteria of a particular application. For photo-electrochemical reductions, cathode 122 may be a p-type semiconductor electrode, such as p-GaAs, p-GaP, p-InN, p-InP, p-CdTe, p-$GaInP_2$ and p-Si, or an n-type semiconductor, such as n-GaAs, n-GaP, n-InN, n-InP, n-CdTe, n-$GaInP_2$ and n-Si. Other semiconductor electrodes may be implemented to meet the criteria of a particular application including, but not limited to, CoS, $MoS_2$, TiB, $WS_2$, SnS, $Ag_2S$, $CoP_2$, $Fe_3P$, $Mn_3P_2$, MoP, $Ni_2Si$, $MoSi_2$, WSi2, $CoSi_2$, $Ti_4O_7$, $SnO_2$, GaAs, GaSb, Ge, and CdSe.

Catholyte may include a pH range from 1 to 12 if an aqueous solvent or electrolyte is employed, preferably from pH 4 to pH 10. The selected operating pH may be a function of any catalysts utilized in operation of the electrochemical cell 102. Preferably, catholyte and catalysts may be selected to prevent corrosion at the electrochemical cell 102. Catholyte may include homogeneous catalysts. Homogeneous catalysts are defined as aromatic heterocyclic amines and may include, but are not limited to, unsubstituted and substituted pyridines and imidazoles. Substituted pyridines and imidazoles may include, but are not limited to mono and disubstituted pyridines and imidazoles. For example, suitable catalysts may include straight chain or branched chain lower alkyl (e.g., C1-C10) mono and disubstituted compounds such as 2-methylpyridine, 4-tertbutyl pyridine, 2,6 dimethylpyridine (2,6-lutidine); bipyridines, such as 4,4'-bipyridine; amino-substituted pyridines, such as 4-dimethylamino pyridine; and hydroxyl-substituted pyridines (e.g., 4-hydroxypyridine) and substituted or unsubstituted quinoline or isoquinolines. The catalysts may also suitably include substituted or unsubstituted dinitrogen heterocyclic amines, such as pyrazine, pyridazine and pyrimidine. Other catalysts generally include azoles, imidazoles, indoles, oxazoles, thiazoles, substituted species and complex multi-ring amines such as adenine, pterin, pteridine, benzimidazole, phenonthroline and the like.

The catholyte may include an electrolyte. Catholyte electrolytes may include alkali metal bicarbonates, carbonates, sulfates, phosphates, borates, and hydroxides. The electrolyte may comprise one or more of $Na_2SO_4$, KCl, $NaNO_3$, NaCl, NaF, $NaClO_4$, $KClO_4$, $K_2SiO_3$, $CaCl_2$, a guanidinium cation, an H cation, an alkali metal cation, an ammonium cation, an alkylammonium cation, a tetraalkyl ammonium cation, a halide anion, an alkyl amine, a borate, a carbonate, a guanidinium derivative, a nitrite, a nitrate, a phosphate, a polyphosphate, a perchlorate, a silicate, a sulfate, and a hydroxide. In one embodiment, bromide salts and acids such as NaBr, KBr, or HBr may be preferred.

The catholyte may further include an aqueous or non-aqueous solvent. An aqueous solvent may include greater than 5% water. A non-aqueous solvent may include as much as 5% water. A solvent may contain one or more of water or a non-aqueous solvent. Representative solvents include methanol, ethanol, acetonitrile, propylene carbonate, ethylene carbonate, dimethyl carbonate, diethyl carbonate, dimethylsulfoxide, dimethylformamide, acetonitrile, acetone, tetrahydrofuran, N,N-dimethylacetaminde, dimethoxyethane, diethylene glycol dimethyl ester, butyrolnitrile, 1,2-difluorobenzene, γ-butyrolactone, N-methyl-2-pyrrolidone, sulfolane, 1,4-dioxane, nitrobenzene, nitromethane, acetic anhydride, ionic liquids, and mixtures thereof.

In one embodiment, a catholyte/anolyte flow rate may include a catholyte/anolyte cross sectional area flow rate range such as 2-3,000 gpm/ft$^2$ or more (0.0076-11.36 m$^3$/m$^2$). A flow velocity range may be 0.002 to 20 ft/sec (0.0006 to 6.1 m/sec). Operation of the electrochemical cell catholyte at a higher operating pressure allows more dissolved carbon dioxide to dissolve in the aqueous solution. Typically, electrochemical cells may operate at pressures up to about 20 to 30 psig in multi-cell stack designs, although with modifications, the electrochemical cells may operate at up to 100 psig. The electrochemical cell may operate anolyte at the same pressure range to minimize the pressure differential on a separator 128 or membrane separating the two regions. Special electrochemical designs may be employed to operate electrochemical units at higher operating pressures up to about 60 to 100 atmospheres or greater, which is in the liquid $CO_2$ and super-critical $CO_2$ operating range.

In another embodiment, a portion of a catholyte recycle stream may be separately pressurized using a flow restriction with backpressure or using a pump, with $CO_2$ injection, such that the pressurized stream is then injected into the catholyte region of the electrochemical cell which may increase the amount of dissolved $CO_2$ in the aqueous solution to improve the conversion yield. In addition, micro-bubble generation of carbon dioxide may be conducted by various means in the catholyte recycle stream to maximize carbon dioxide solubility in the solution.

Catholyte may be operated at a temperature range of −10 to 95° C., more preferably 5-60° C. The lower temperature will be limited by the catholytes used and their freezing points. In general, the lower the temperature, the higher the solubility of $CO_2$ in an aqueous solution phase of the catholyte, which would help in obtaining higher conversion and current efficiencies. The drawback is that the operating electrochemical cell voltages may be higher, so there is an optimization that would be done to produce the chemicals at the lowest operating cost. In addition, the catholyte may require cooling, so an external heat exchanger may be employed, flowing a portion, or all, of the catholyte through the heat exchanger and using cooling water to remove the heat and control the catholyte temperature.

Anolyte operating temperatures may be in the same ranges as the ranges for the catholyte, and may be in a range of 0° C. to 95° C. In addition, the anolyte may require cooling, so an external heat exchanger may be employed, flowing a portion, or all, of the anolyte through the heat exchanger and using cooling water to remove the heat and control the anolyte temperature.

Electrochemical cells may include various types of designs. These designs may include zero gap designs with a finite or zero gap between the electrodes and membrane, flow-by and flow-through designs with a recirculating catholyte electrolyte utilizing various high surface area cathode materials. The electrochemical cell may include flooded co-current and counter-current packed and trickle bed designs with the various high surface area cathode materials. Also, bipolar stack cell designs and high pressure cell designs may also be employed for the electrochemical cells.

Anode electrodes may be the same as cathode electrodes or different. Anode 126 may include electrocatalytic coatings applied to the surfaces of the base anode structure. Anolytes may be the same as catholytes or different. Anolyte electrolytes may be the same as catholyte electrolytes or different. Anolyte may comprise solvent. Anolyte solvent may be the same as catholyte solvent or different. For example, for HBr, acid anolytes, and oxidizing water generating oxygen, the preferred electrocatalytic coatings may include precious metal oxides such as ruthenium and iridium oxides, as well as platinum and gold and their combinations as metals and oxides on valve metal substrates such as titanium, tantalum, zirconium, or niobium. For bromine and iodine anode chemistry, carbon and graphite are particularly suitable for use as anodes. Polymeric bonded carbon material may also be used. For other anolytes, comprising alkaline or hydroxide electrolytes, anodes may include carbon, cobalt oxides, stainless steels, transition metals, and their alloys and combinations. High surface area anode structures that may be used which would help promote the reactions at the anode surfaces. The high surface area anode base material may be in a reticulated form composed of fibers, sintered powder, sintered screens, and the like, and may be sintered, welded, bonded, or mechanically connected to a current distributor back plate that is commonly used in bipolar electrochemical cell assemblies. In addition, the high surface area reticulated anode structure may also contain areas where additional applied catalysts on and near the electrocatalytic active surfaces of the anode surface structure to enhance and promote reactions that may occur in the bulk solution away from the anode surface such as the reaction between bromine and the carbon based reactant being introduced into the anolyte. The anode structure may be gradated, so that the density of the may vary in the vertical or horizontal direction to allow the easier escape of gases from the anode structure. In this gradation, there may be a distribution of particles of materials mixed in the anode structure that may contain catalysts, such as metal halide or metal oxide catalysts such as iron halides, zinc halides, aluminum halides, cobalt halides, for the reactions between the bromine and the carbon-based reactant. For other anolytes comprising alkaline, or hydroxide electrolytes, anodes may include carbon, cobalt oxides, stainless steels, and their alloys and combinations.

Separator 128, also referred to as a membrane, between first region 120 and second region 122, may include cation ion exchange type membranes. Cation ion exchange membranes, which have a high rejection efficiency to anions, may be preferred. Examples of such cation ion exchange membranes may include perfluorinated sulfonic acid based ion exchange membranes such as DuPont Nafion® brand unreinforced types N117 and N120 series, more preferred PTFE fiber reinforced N324 and N424 types, and similar related membranes manufactured by Japanese companies under the supplier trade names such as AGC Engineering (Asahi Glass) under their trade name Flemion®. Other multi-layer perfluorinated ion exchange membranes used in the chlor alkali industry may have a bilayer construction of a sulfonic acid based membrane layer bonded to a carboxylic acid based membrane layer, which efficiently operates with an anolyte and catholyte above a pH of about 2 or higher. These membranes may have a higher anion rejection efficiency. These are sold by DuPont under their Nafion® trademark as the N900 series, such as the N90209, N966, N982, and the 2000 series, such as the N2010, N2020, and N2030 and all of their types and subtypes. Hydrocarbon based membranes, which are made from of various cation ion exchange materials may also be used if the anion rejection is not as desirable, such as those sold by Sybron under their trade name Ionac®, AGC Engineering (Asahi Glass) under their Selemion® trade name, and Tokuyama Soda, among others on the market. Ceramic based membranes may also be employed, including those that are called under the general name of NASICON (for sodium super-ionic conductors) which are chemically stable over a wide pH range for various chemicals and selectively transports sodium ions, the composition is $Na_{1+x}Zr_2Si_xP_3-xO_{12}$, and well as other ceramic based conductive membranes based on titanium oxides, zirconium oxides and yttrium oxides, and beta aluminum oxides. Alternative membranes that may be used are those with different structural backbones such as polyphosphazene and sulfonated polyphosphazene membranes in addition to crown ether based membranes. Preferably, the membrane or separator is chemically resistant to the anolyte and catholyte and operates at temperatures of less than 600 degrees C., and more preferably less than 500 degrees C.

Figure 5:
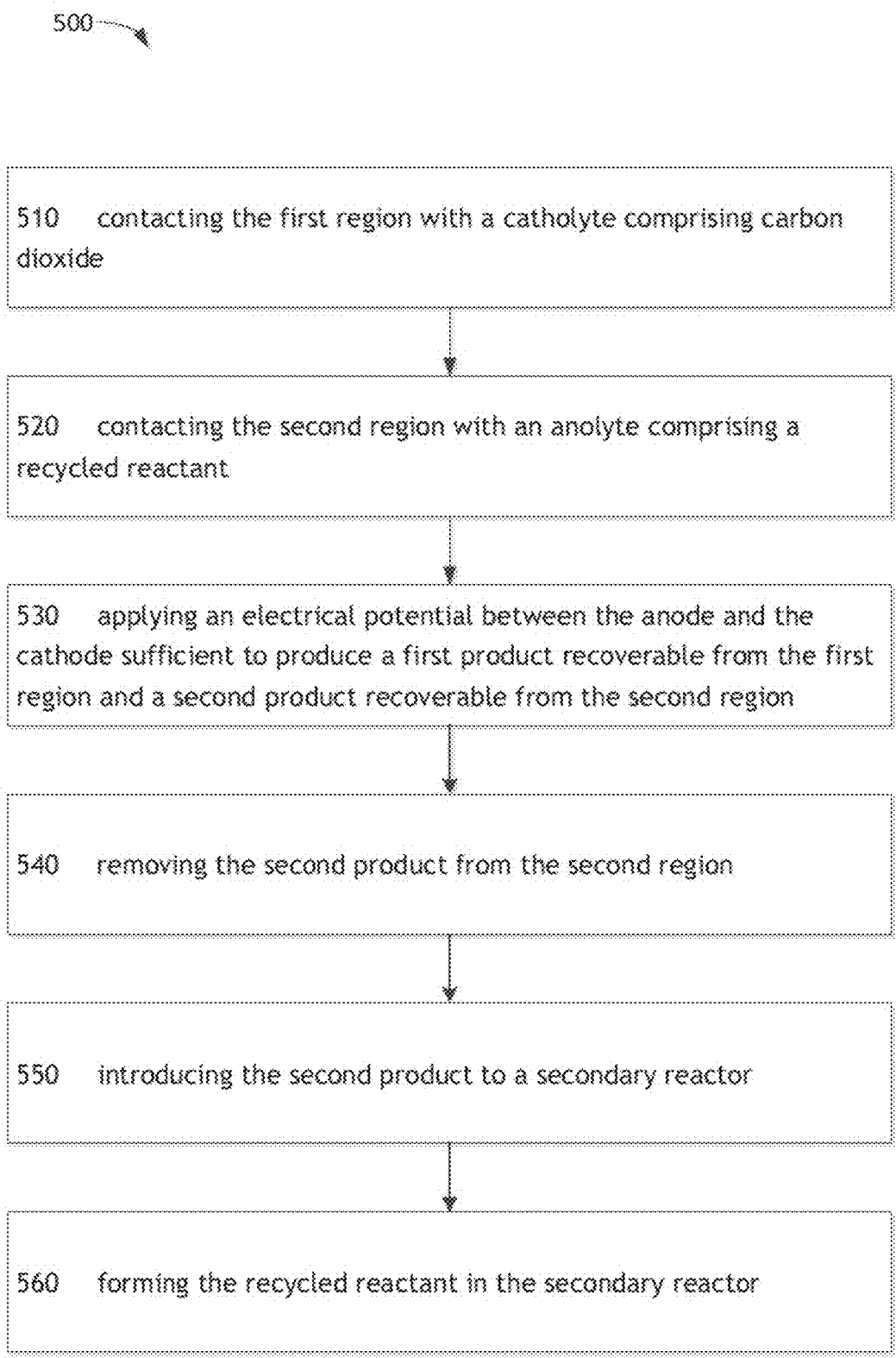
FIG. 5 is a flow diagram of a method of electrochemical co-production of products in accordance with an embodiment of the present disclosure.

Referring to FIG. 5 a flow diagram of a method 500 of electrochemical co-production of products in accordance with an embodiment of the present disclosure is shown. It is contemplated that method 500 may be performed by system 100 and system 200 as shown in FIGS. 1-2. Method 500 may include producing a first product from a first region of an electrochemical cell having a cathode and a second product from a second region of the electrochemical cell having an anode.

Method 500 of electrochemical co-production of products may include a step of contacting the first region with a catholyte comprising carbon dioxide 510. Next, method 500 may include contacting the second region with an anolyte comprising a recycled reactant 520. Method 500 may further include applying an electrical potential between the anode and the cathode sufficient to produce a first product recoverable from the first region and a second product recoverable from the second region 530. Method 500 may additionally include removing the second product from the second region 540. Method 500 may additionally include introducing the second product to a secondary reactor 550. Further, method 500 may include forming the recycled reactant in the secondary reactor 560. Advantageously, a first product produced at the first region may be recoverable from the first region and the recycled reactant produced in the secondary reactor may be recycled to the second region.

Figure 6:
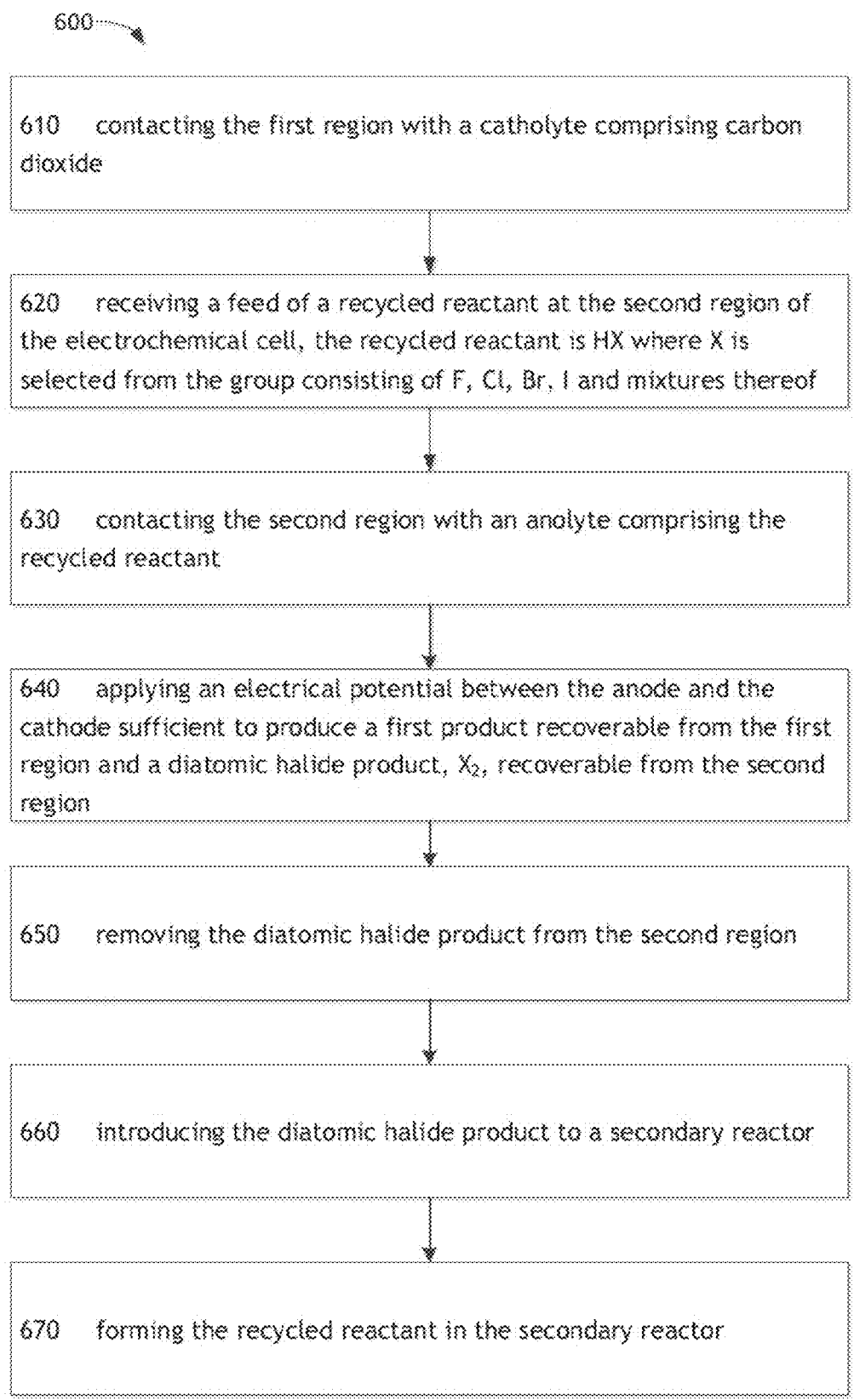
FIG. 6 is a flow diagram of a method of electrochemical co-production of products in accordance with another embodiment of the present disclosure.

Referring to FIG. 6 a flow diagram of a method 600 of electrochemical co-production of products in accordance with an embodiment of the present disclosure is shown. It is contemplated that method 600 may be performed by system 100 and system 200 as shown in FIGS. 1-2. Method 600 may include producing a first product from a first region of an electrochemical cell having a cathode and a second product from a second region of the electrochemical cell having an anode.

Method 600 of electrochemical co-production of products may include a step of contacting the first region with a catholyte comprising carbon dioxide 610. Next, method 600 may include receiving a feed of a recycled reactant at the second region of the electrochemical cell, the recycled reactant is HX where X is selected from the group consisting of F, Cl, Br, I and mixtures thereof 620. Method 600 may further include contacting the second region with an anolyte comprising the recycled reactant 630. Method 600 may additionally include applying an electrical potential between the anode and the cathode sufficient to produce a first product recoverable from the first region and a diatomic halide product, $X_2$, recoverable from the second region 640. Method 600 may additionally include removing the diatomic halide product from the second region 650. Further, method 600 may include introducing the diatomic halide product to a secondary reactor 660. Method 600 may also include forming the recycled reactant in the secondary reactor 670. Advantageously, a first product produced at the first region may be recoverable from the first region and the recycled reactant produced in the secondary reactor may be recycled to the second region.

Figure 7:
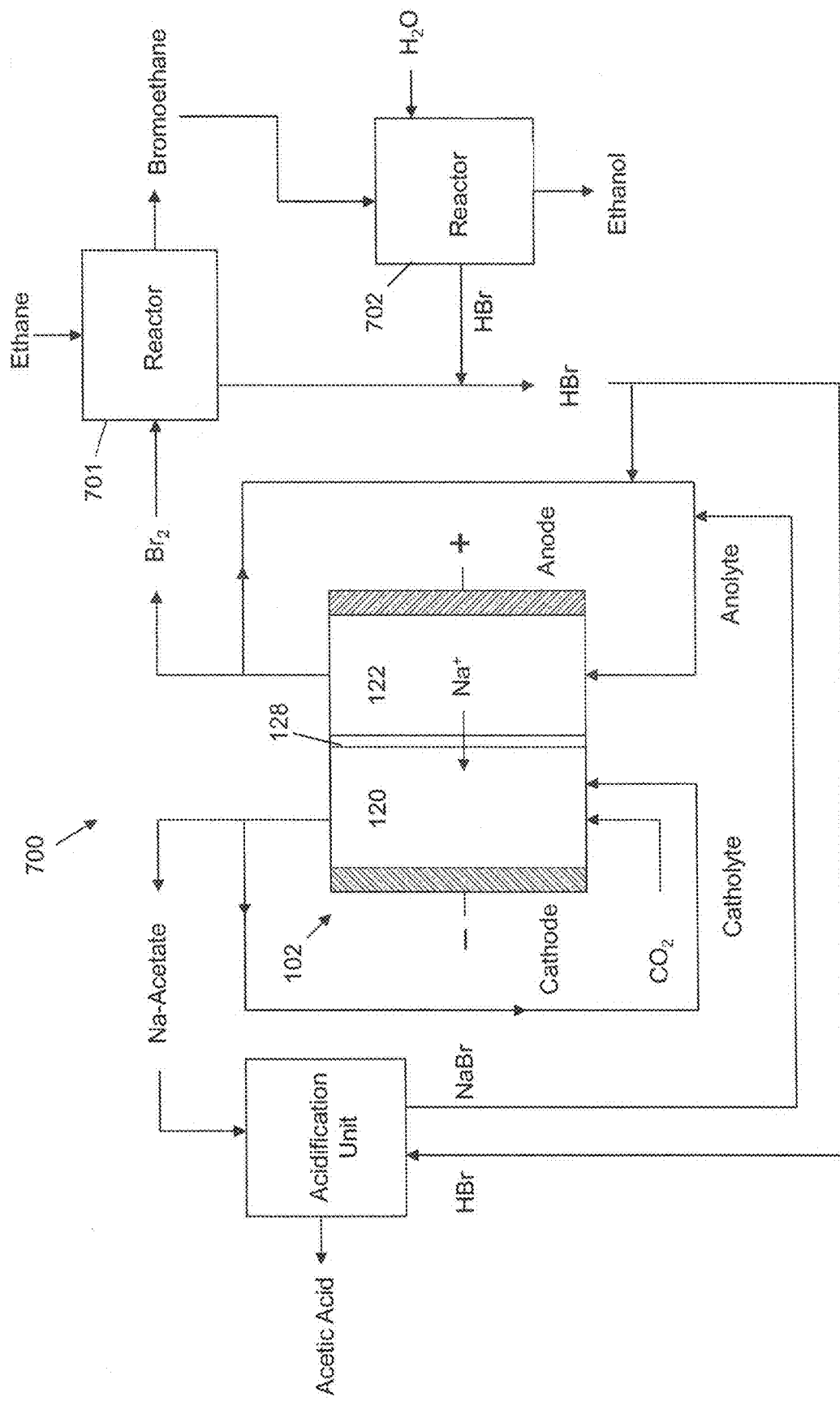
FIG. 7 is a block diagram of a system in accordance with an additional embodiment of the present disclosure.
Figure 8:
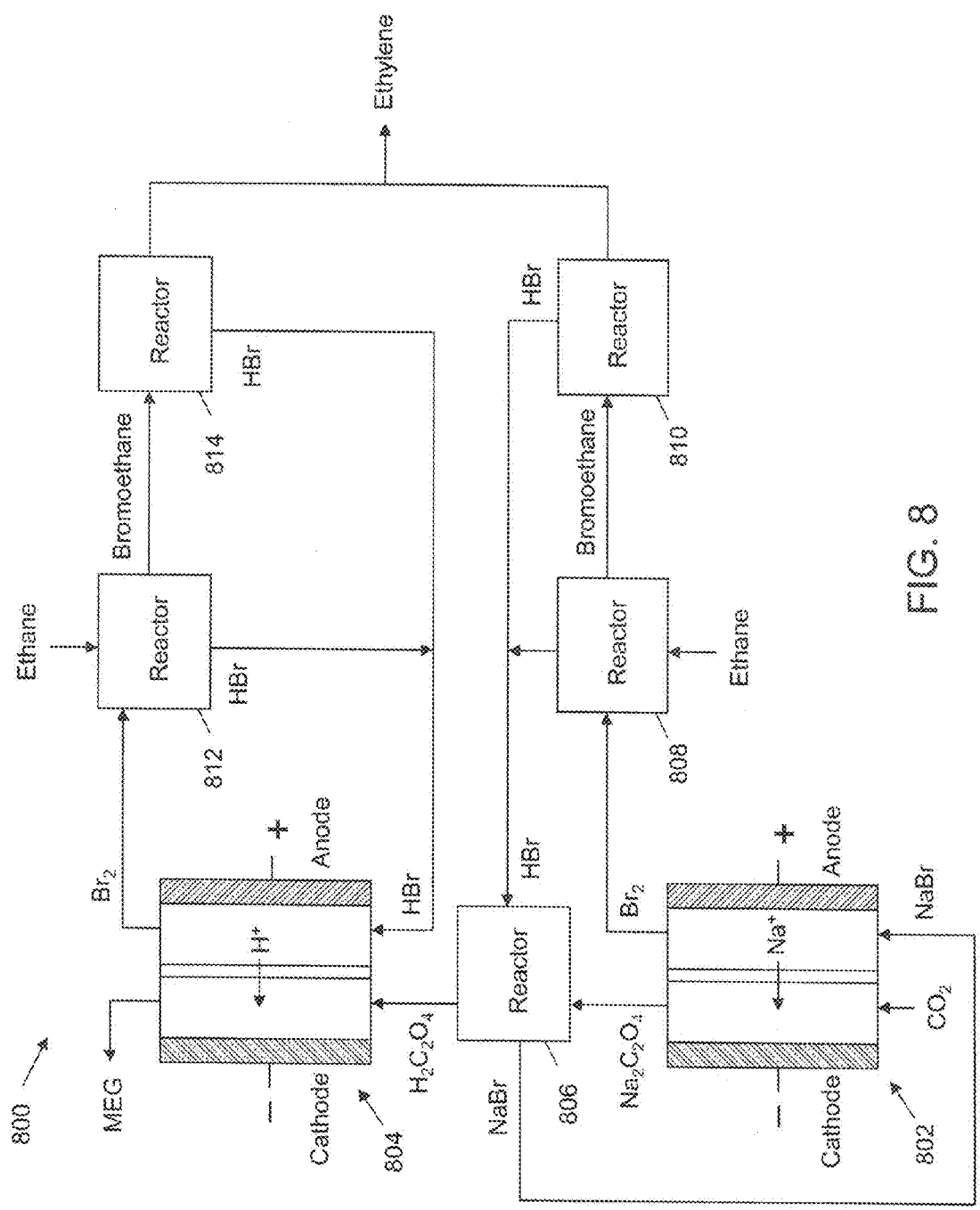
FIG. 8 is a block diagram of a system in accordance with an additional embodiment of the present disclosure.

Referring now to FIG. 7, an embodiment of an electrochemical system 700 For the co-production of acetic acid and ethanol is shown. The overall equation for the desired reaction may be $2CO_2+4C_2H_6+2H_2O \rightarrow CH_3COOH+4C_2H_5OH$. HBr is introduced to the second region 122 of a two compartment cell 102 having first region 120 and second region 122 that is separated by cation exchange membrane 128. HBr may be circulated with a pump in an anolyte circulation loop where HBr may be converted to $Br_2$ as a gas or liquid in the second region, where $Na^+$ ions crossing the membrane 128 into the first region 120. Alternatively, $Br_2$ may be collected as a liquid stream containing $HBr_3$, (i.e., bromine combined with HBr), which may serve as an oxidizer for the formation of bromoethane from the reaction of bromine with ethane in reactor 701, which may then be converted to ethanol using a reaction with water or alkali hydroxide in reactor 702.

On the cathode side in first region 120, carbon dioxide is reacted on a high surface area cathode to produce, in this example, sodium acetate. A circulation pump may be used to provide sufficient mass transfer to obtain a high Faradaic efficiency conversion to acetate. The product acetate overflows the catholyte loop, and may be converted to the acid form in the acidification unit using either an electrochemical acidification unit or by direct mixing with HBr and may be then purified and concentrated in a separate unit (not shown).

The electrochemical cell may be operated at a current density of greater than 3 kA/m² (300 mA/cm²), or in suitable range of 0.5 to 5 kA/m² or higher if needed. The current density of the formation of bromine from HBr may easily be operated at even higher current densities. The cell may be operated in a liquid phase in both the anode and cathode compartments, or in a preferred embodiment, may be liquid phase in the cathode compartment with a gas phase anode compartment wherein gas phase HBr is fed directly to the anode.

The operating voltage of the system at a current density of 1 kA/m² may be between 1.0-2.5 volts, where the half cell voltage of anolyte reaction may be between 0.6V and 1.2V. In comparison, the comparable cell voltage using a 1 M sulfuric acid anolyte with the formation of oxygen operating at 1 kA/m² may likely be between 2.0V and 4V.

In the case of a liquid anolyte, the HBr anolyte concentration may be in the range of 5 wt % to 50 wt %, more preferably in the range of 10 wt % to 40 wt %, and more preferably in the 15 wt % to 30 wt % range, with a corresponding 2 to 30 wt % bromine content as $HBr_3$ in the solution phase. The HBr content in the anolyte solution may control the anolyte solution conductivity, and thus the anolyte compartment IR voltage drop. If the anode is run with gas phase HBr, then HBr concentrations will approach 100% by wt % in anhydrous conditions.

The anode may preferably include a polymeric bound carbon current distributor anode and incorporate a high surface area carbon felt with a specific surface area of 50 cm²/cm³ or more that fills the gap between the cathode back plate and the membrane, thus having a zero gap anode. Metal and/or metal oxide catalysts may be added to the anode in order to decrease anode potential and/or increase anode current density. An example is the use of a $RuO_2$ catalyst.

The cathode may also be a number of high surface area materials, which may include copper, stainless steels, carbon, and silicon, which may be further coated with a layer of material which may be a conductive metal or semiconductor. There is a very thin plastic screen against the cathode side of the membrane to prevent the membrane from touching the high surface area cathode structure. The high surface area cathode structure is mechanically pressed against the cathode current distributor backplate, which may be composed of material that has the same surface composition as the high surface area cathode.

The operating Faradaic current efficiency of the anode may preferably between 90 to 100%, and the acetate Faradaic current efficiency may preferably be between 25 and 100%. The flow circulation of the anolyte and catholyte may be such that it provides sufficient flow for the reactions.

$Br_2$ produced at the anode in second region 122 may be reacted with ethane to make bromoethane and HBr. The bromoethane may then be reacted with water to form ethanol and HBr. Though high selectivity for bromoethane may be generally observed, the reaction product may contain up to 15% byproduct of dibromoethane (1,1 dibromoethane and/or 1,2 dibromoethane). These byproducts may be sold or chemically converted into a non-Br containing compound such as acetylene or acetaldehyde in order to reclaim the Br. These byproducts may also be catalytically converted into 1-bromoethane or hydrogenated back to ethane. The reaction of bromoethane to ethanol may be catalyzed by a base such as NaOH, by magnesium or similar metals that have a high affinity for Br, or by a zeolite containing metal reaction sites. The HBr byproduct from the reactors making bromoethane and ethanol may be recycled back to the anode portion of the cell. Br is thus conserved and H is made available for $CO_2$ reduction.

What is claimed is:

1. A method for producing a first product from a first region of an electrochemical cell having a cathode and a second product from a second region of the electrochemical cell having an anode, the method comprising the steps of:
    contacting the first region with a catholyte comprising carbon dioxide;
    contacting the second region with an anolyte comprising a recycled reactant, wherein the recycled reactant is a hydrogen halide, HX, where X is selected from the group consisting of F, Cl, Br, I, and mixtures thereof;
    applying an electrical potential between the anode and the cathode sufficient to produce the first product from the first region and the second product from the second region, wherein the second product is $X_2$;
    removing the second product from the second region;
    introducing the second product and at least one of an alkane, an alkene or an aromatic compound to a secondary reactor;
    producing the recycled reactant through a reaction of the second product and the at least one of an alkane, an alkene or an aromatic compound; and
    recycling the recycled reactant produced through the reaction of the second product and the at least one of an alkane, an alkene or an aromatic compound at the secondary reactor to the second region.

2. The method according to claim 1, further comprising:
    forming a halogenated organic compound in the secondary reactor.

3. The method according to claim 2, further comprising:
    feeding the halogenated organic compound into a third reactor.

4. The method according to claim 3, further comprising:
    feeding water into the third reactor.

5. The method according to claim 4, further comprising:
    forming an alcohol and HX in the third reactor; and
    recycling the HX into the second region.

6. The method according to claim 3, further comprising:
    forming HX and at least one of an alkene and an alkyne in the third reactor; and
    recycling the HX into the second region.

7. The method according to claim 3, further comprising:
    forming HX and at least one of an alcohol, an alkene, an alkyne, an aldehyde, a ketone, an alkane, and mixtures thereof in the third reactor; and
    recycling the HX into the second region.

8. The method according to claim 2, wherein the halogenated organic compound is bromoethane.

9. The method according to claim 1, wherein HX is HBr.

10. The method according to claim 9, wherein the second product is $Br_2$.

11. The method according to claim 1, wherein the anolyte and catholyte further comprise water, the first product includes acetic acid, and the $X_2$ is $Br_2$.

12. The method according to claim 1, wherein the catholyte further comprises a non-aqueous solvent, the first product includes a carboxylic acid, and the $X_2$ is $Br_2$.

13. The method according to claim 1, wherein the first region and the second region are separated by an ion permeable barrier that operates at a temperature of less than 600 degrees C.

14. The method according to claim 13, wherein the ion permeable barrier includes one of a polymeric or inorganic ceramic-based ion permeable barrier.

15. The method according to claim 1, wherein the catholyte is a liquid and the anolyte is a gas.

16. The method according to claim 1, wherein the catholyte is a liquid and the anolyte is a liquid.

17. The method according to claim 1, wherein said first product includes at least one of carbon monoxide, formic acid, formaldehyde, methanol, methane, oxalate, oxalic acid, glyoxylic acid, glyoxylate, glycolic acid, glyco late, glyoxal, glycolaldehyde, ethylene glycol, acetic acid, acetate, acetaldehyde, ethanol, ethane, ethylene, lactic acid, lactate, propionic acid, propionate, acetone, isopropanol, 1-propanol, 1,2-propylene glycol, propane, propylene, butane, butene, 1-butanol, 2-butanone, 2-butanol, a carboxylic acid, a carboxylate, a ketone, an aldehyde, and an alcohol.

18. The method according to claim 1, wherein the catholyte further comprises a solvent selected from the group consisting of water, methanol, ethanol, acetonitrile, propylene carbonate, ethylene carbonate, dimethyl carbonate, diethyl carbonate, dimethylsulfoxide, dimethylformamide, acetonitrile, acetone, tetrahydrofuran, N,N-dimethylacetaminde, dimethoxyethane, diethylene glycol dimethyl ester, butyrolnitrile, 1,2-difluorobenzene, γ-butyrolactone, N-methyl-2-pyrrolidone, sulfolane, 1,4-dioxane, nitrobenzene, nitromethane, acetic anhydride, ionic liquids, and mixtures thereof.

* * * * *